(12) United States Patent
Deily et al.

(10) Patent No.: US 6,284,179 B1
(45) Date of Patent: Sep. 4, 2001

(54) METHOD OF MANUFACTURING A NECK FLANGE

(75) Inventors: Michael Deily, Tustin; Norman Crandall, Costa Mesa, both of CA (US)

(73) Assignee: Mallinckrodt Medical Inc., St. Louis, MO (US)

( * ) Notice: Subject to any disclaimer, the term of this patent is extended or adjusted under 35 U.S.C. 154(b) by 0 days.

(21) Appl. No.: 08/463,383

(22) Filed: Jun. 5, 1995

Related U.S. Application Data

(60) Division of application No. 07/993,718, filed on Dec. 16, 1992, now Pat. No. 5,819,734, which is a continuation-in-part of application No. 07/763,836, filed on Sep. 23, 1991, now abandoned.

(51) Int. Cl.[7] .............................. B29C 45/14; B29C 70/74
(52) U.S. Cl. .......................... 264/254; 264/255; 264/267
(58) Field of Search .................................. 264/250, 252, 264/254, 255, 259, 271.1, 275, 294, 247, 267

(56) References Cited

U.S. PATENT DOCUMENTS

| | | | |
|---|---|---|---|
| 3,659,612 | * | 5/1972 | Shiley et al. .......................... 128/351 |
| 3,693,624 | * | 9/1972 | Shiley et al. .......................... 128/351 |
| 4,033,353 | * | 7/1977 | La Rosa ................................ 128/351 |
| 4,040,670 | * | 8/1977 | Williams .............................. 264/255 |
| 4,269,802 | * | 5/1981 | Linne .................................. 264/255 |
| 4,315,505 | * | 2/1982 | Crandall et al. ................. 128/200.26 |
| 4,332,245 | * | 6/1982 | Boone, Sr. ...................... 128/207.17 |
| 4,536,116 | * | 8/1985 | Murray ................................. 264/274 |
| 4,906,234 | * | 3/1990 | Voychehovski ......................... 604/79 |
| 5,472,655 | * | 12/1995 | Morita ................................. 264/250 |
| 5,481,763 | * | 1/1976 | Brostrom et al. ..................... 264/252 |

* cited by examiner

Primary Examiner—Angela Ortiz
(74) Attorney, Agent, or Firm—David A. Hey

(57) ABSTRACT

A neck flange supports a tracheostomy tube inserted into the neck and has a neck engaging portion of a molded thin flexible flat sheet of a transparent polymer. An interconnection positioned centrally within the neck engaging portion and carried thereby has a ring shaped body with an opening and a pair of opposed pivot pins extending inwardly into the opening for carrying the tube passing therethrough. The pair of opposed pins fit for movement within recesses in the tube to permit limited swivel motion. The interconnection is molded of a transparent polymer material that is less flexible than the neck engaging portion and has a stepped cross section so the pair of opposed pivot pins are raised relative to the ring shaped body. The neck engaging portion is molded about the interconnection so the raised pair of opposed pins remain exposed. A method for manufacturing the neck flange has the steps of molding a ring shaped interconnection of a polymer and molding a neck engaging portion about the interconnection by inserting the interconnection into a mold then molding the neck engaging portion thereabout. A method for using the neck flange has the steps of placing the tracheostomy tube in a patient's neck and swiveling the neck engaging portion relative the tube to conform to the neck flexing the neck engaging portion to conform to the curvature of the neck and observing the condition of the neck under the transparent neck flange.

2 Claims, 4 Drawing Sheets

METHOD OF MANUFACTURING A NECK FLANGE

Related Patent Application

This application is a division of U.S. patent application Ser. No. 07/993,718, filed Dec. 16, 1992, now U.S. Pat. No. 5,819,734 which is a continuation-in-part of U.S. patent application Ser. No. 07/763,836, filed Sep. 23, 1991 now abandoned.

FIELD OF THE INVENTION

This invention relates to a neck flange for a tracheostomy tube that provides comfort and adjustability when used to secure the tracheostomy tube to the patient's neck. The neck flange has a neck engaging portion made of a flexible material and an interconnection positioned centrally within it that is made of a material less flexible than the neck engaging portion. The interconnection supports a tracheostomy cannula having a restricted motion substantially within a plane generally normal to the neck engaging portion. The flexible and less flexible materials are molded by the step of preparing a part from one material and then insert molding the other material over it. They may be made of transparent materials.

BACKGROUND OF THE DISCLOSURE

Flexible neck flanges or flanges with pivotal joints to mount them to the tracheostomy tube are commercially available. U.S. Pat. Nos. 3,659,612 and 3,693,624 employ a neck flange of a flat plastic material pivotally connected to a tracheostomy tube. The tracheostomy tube and the neck flange are movably connected by pivots on the neck flange that fit into recesses in the tracheostomy tube. U.S. Pat. No. 4,033,353 describes a neck flange made of a flexible material to which a tracheostomy tube is mounted by flexible portions thereof. Specifically, thin webs of neck flange material between the tracheostomy tube and the part of the flange that is to be secured to the patient's neck provide the flexible portion.

U.S. Pat. No. 4,906,234 has a holder for medical tubes that provides axial adjustment along the tube for placement of an endotracheal tube within different areas of the oral cavity. A band fitted around the head cooperates with a releasable anchor so the holder may be laterally adjusted. The patent has no description for adapting the device to the curvature near the oral cavity of the patient. An endotracheal tube has no percutaneous intrusion and is not intended to be fitted to the human neck.

U.S. Pat. No. 4,332,245 has a neck flange with J-shaped clips that hooks onto a retention member that fits around the patient's neck. The neck flange and an integrated tube are made of the same material. In this device, flexibility is dependent on wall thickness and not the physical properties of the materials of construction.

U.S. Pat. No. 4,315,505 has a tracheostomy tube with a molded external end designed to receive a disposable inner cannula to facilitate cleaning. The molded end includes recesses to receive pins on the neck flange. This allows pivotal movement between the tube and the neck flange. The neck flange must be rigid enough to retain the position of the pins and maintain the pins in their respective recesses. This design makes examination of the neck below the inserted inner cannula tube difficult.

The art fails to disclosure a neck flange with a neck engaging portion that is made of a flexible material and an interconnection positioned centrally within the neck engaging portion made of a material that is less flexible. The art fails to suggest neck flanges made of transparent materials or neck flanges made by insert molding.

SUMMARY OF THE INVENTION

This invention relates to a tracheostomy tube containing a neck flange comprising a neck engaging portion and an interconnection positioned within the neck engaging portion. The neck engaging portion is more flexible than the interconnection. This difference in flexibility stems from their respective materials of construction. The neck engaging portion is made of a material that is more flexible than the material used in making the interconnection. The interconnection carries a tracheostomy tube outer cannula for limited movement relative to the neck engaging portion. The interconnection within the neck engaging portion is made by insert molding. The manner of molding of the neck flange and/or its parts of transparent materials are one of the improvements provided by the invention. This feature of the invention allows medical practitioners to observe entry of the tube into the patients neck.

The neck flange for the tracheostomy tube positions and supports the tube. The tube is inserted into the neck of a human. The neck flange preferably includes a neck engaging portion comprises a thin flexible flat sheet with a pair of essentially parallel major surfaces defined by edges therearound and an aperture in it that is generally centrally located. The neck engaging portion is most preferably molded of a flexible, transparent polymer material.

Affixed centrally in the neck engaging portion is the interconnection. The interconnection is a ring-shaped body with an opening and a pair of opposed pivot pins extending into the opening for carrying the tracheostomy tube passing therethrough. The pair of opposed pins are preferably held f or movement in respective recesses in the tracheostomy tube thus permitting limited swivel-motion thereof substantially within a plane generally normal to one major surface of the neck engaging portion.

The interconnection is most preferably molded of a transparent polymer material less flexible than the neck engaging portion and has a stepped cross section so the pair of opposed pivot pins are raised relative to the ring shaped body. The neck engaging portion may preferably be molded of a polymer about the interconnection and the raised pair of opposed pins remain exposed. The interconnection is perhaps molded of a polymer having a durometer of approximately 70–100 85 Shore D per ASTM D-785 and the durometer of the neck engaging portion may have a durometer in the range of approximately 85 or 90 Shore A per ASTM D-2240.

The method of manufacture of a neck flange having a neck engaging portion of a flexible material and an interconnection of a less flexible material includes the steps of molding a ring shaped interconnection of a relatively rigid polymer and overmolding a neck engaging portion about the interconnection in a process that may require inserting the ring shaped interconnection into a mold before molding the neck engaging portion thereabout. The method may include the step of selecting polymers that are flexible so that the neck engaging portion is more flexible than the ring shaped interconnection.

The method for using a neck flange for a tracheostomy tube with a neck engaging portion of a flexible material and an interconnection of a less flexible material most preferably has the steps of placing the tracheostomy tube into an entry in a patient's neck and swiveling the neck engaging portion relative to the tracheostomy tube so as to conform the neck engaging portion to the patient's neck. Those steps may be followed by flexing the neck engaging portion to conform to the curvature surrounding the opening in the patient's neck and observing the condition of the entry into the neck under the transparent interconnection or the transparent neck engaging portion.

DETAILED DESCRIPTION OF THE INVENTION

A neck flange for a tracheostomy tube includes a neck engaging portion of a flexible material and methods of manufacture and use thereof. The claims are not limited to the structure for the neck flange described and illustrated by way of example and the methods of manufacture or use specifically explained. The claims are to be considered in view of the existing knowledge of skilled artisans in the Field of the Invention prior to the inventions defined by the language of the claims herein.

Figure 1:
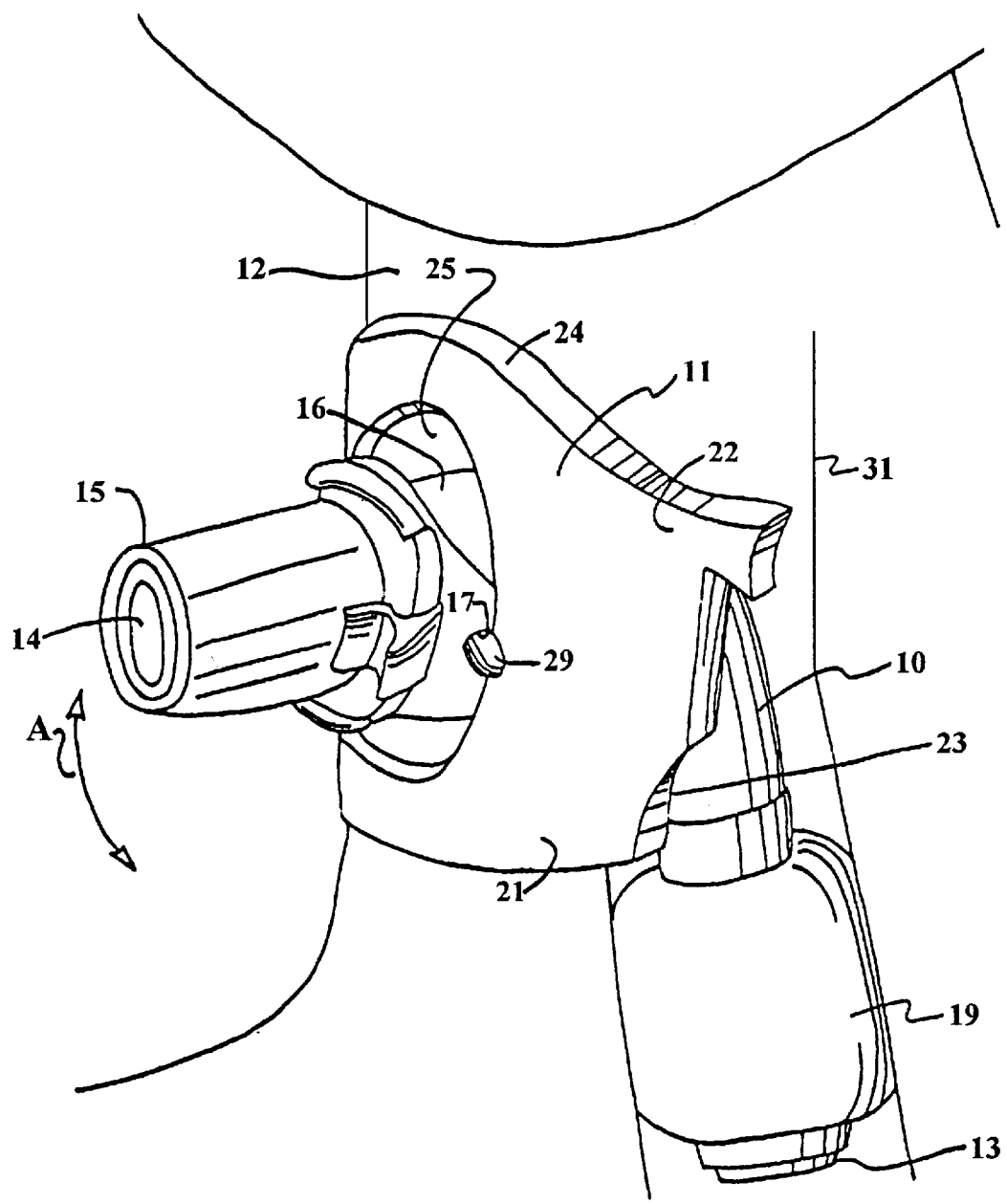
FIG. 1 is a perspective view of a neck flange of the preferred embodiment shown with a tracheostomy tube in position against and within the patient's neck and, for clarity, part of the neck and neck flange is sectioned away.

FIG. 1 is a perspective view of a tracheostomy tube 10 and neck flange 11 of the preferred embodiment shown with the tracheostomy tube 10 in position against and within the patient's neck 12 and for clarity of illustration part of the neck 12 is shown removed. The tracheostomy tube 10 and neck flange 11 may be used with a tracheotomy procedure on the neck 12 of a human. The tracheostomy tube 10 has a distal end 13 for placement in the neck 12 of the patient to form a passage 14 from the proximal end 15 open to an air source to aid breathing. The tracheostomy tube 10 includes a proximal end 15 positioned outside the human's neck 12 when the tracheostomy tube 10 is in place for use. A central part 16 is between the ends 13, 15 of the tracheostomy tube 10. The central part 16 includes recesses 17 on opposite sides thereof across from one another.

Figure 2:
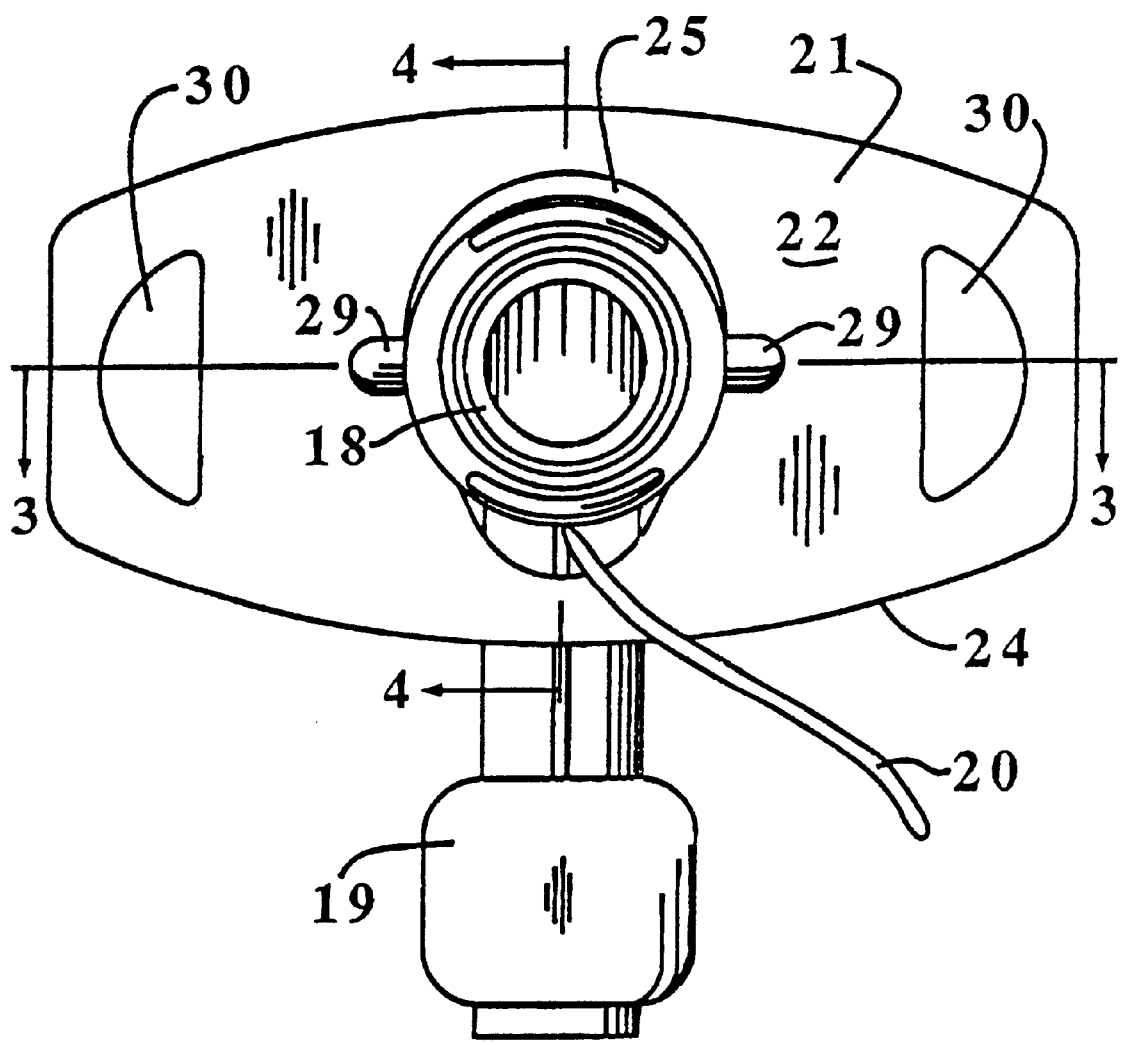
FIG. 2 is a front end view of the preferred neck flange and a tracheostomy tube is shown in combination with an inner cannula and cuff with its inflation tube.

FIG. 2 is a front end view of the preferred neck flange 11 and the tracheostomy tube 10 is shown including an inner cannula 18 and cuff 19 with its inflation tube 20. As can be seen in FIGS. 1 and 2 the neck flange 11 has a neck engaging portion 21 made of a thin flexible sheet, preferably flat but may be curved, with a pair of generally parallel major surfaces 22, 23 defined by an edge 24 therearound and a generally central aperture 25 therethrough. The neck engaging portion 21 of the preferred embodiment is molded of a flexible, transparent polymer material.

Figure 3:
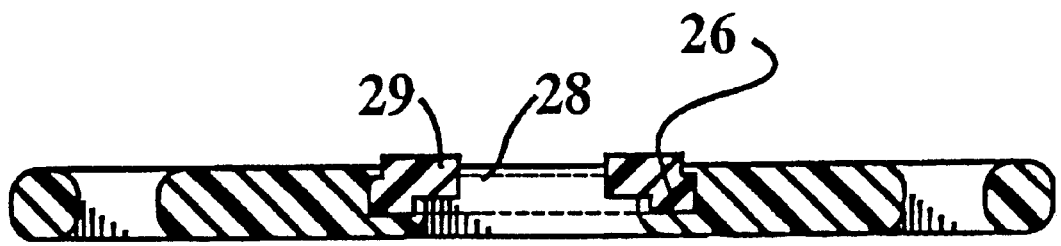
FIG. 3 is a side view in cross section of the neck flange of FIG. 2 as would be seen if the cross section were taken along line 3—3 in FIG. 2 and the tracheostomy tube were not included.

The preferred polymer material should have a durometer hardness of less than 85 Shore A, as measured per ASTM D-2240. A durometer hardness in the range of 70 to 85 Shore A with a minimum tensile strength of 2000 psi as measured per ASTM D-638 is desired. Polymers such as polyvinylchloride, polyurethane or other flexible transparent medical grade polymers may be used for molding the neck engaging portion 21. The particular polymer selected should preferably have additives to maintain the relative transparency during and after sterilization by retort, gas or radiation of up to 3.5 rads. FIG. 3 is a side view in cross section of the neck flange 11 of FIG. 2 as would be seen if the cross section were taken along line 3—3 in FIG. 2 with the tracheostomy tube 10 removed or not shown. An interconnection 26 is positioned centrally within the neck engaging portion 21 and carried thereby as shown in FIG. 3. The interconnection 26 has a ring shaped body 27 with an opening 28 centered therein as best understood by examination of FIGS. 3, 4 and 5. A pair of opposed pivot pins 29 extend toward one another in a radial direction inwardly into the opening 28 for carrying the central part 16 of the tracheostomy tube passing therethrough as illustrated in FIGS. 1 and 2.

As best seen in FIG. 3, the interconnection 26 has a stepped cross section with the pair of opposed pivot pins 29 raised relative to the ring shaped body 27. The pair of opposed pins 29 are arranged to be fit for movement within respective recesses 17 in the tracheostomy tube 10 for permitting limited swivel motion thereof as depicted by arcuate arrows A in FIG. 1 and substantially within a plane generally normal to major surface 22 of the neck engaging portion.

The interconnection 26 is molded of a transparent polymer material of a durometer less flexible than the neck engaging portion 21. The preferred polymer material for the interconnection 26 should have a durometer hardness of about 85 Shore D, as measured per ASTM D-785 and an Izod notched of at least 4.0 ft lb/in. tested per ASTM D-256. Polymers, which are relatively strong, rigid and non-yielding, such as polycarbonate or other transparent medical grade polymers are useful for the interconnection 26. The polymer selected should preferably have additives to maintain the relative transparency during and after sterilization by retort, gas or radiation of up to 3.5 rads.

Figure 4:
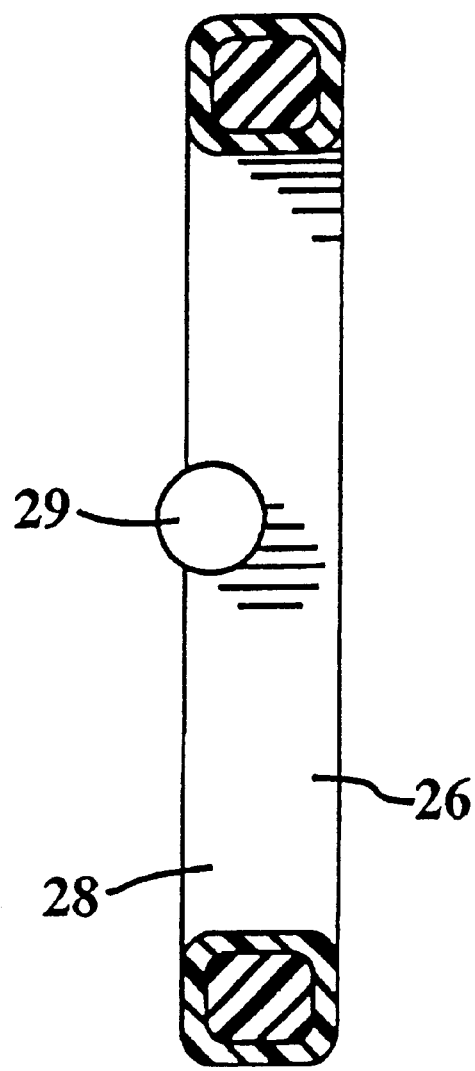
FIG. 4 is a side view in cross section of the neck flange of FIG. 3 or as would be seen if the cross section were taken along line 4—4 in FIG. 3 and the tracheostomy tube were not included.
Figure 5:
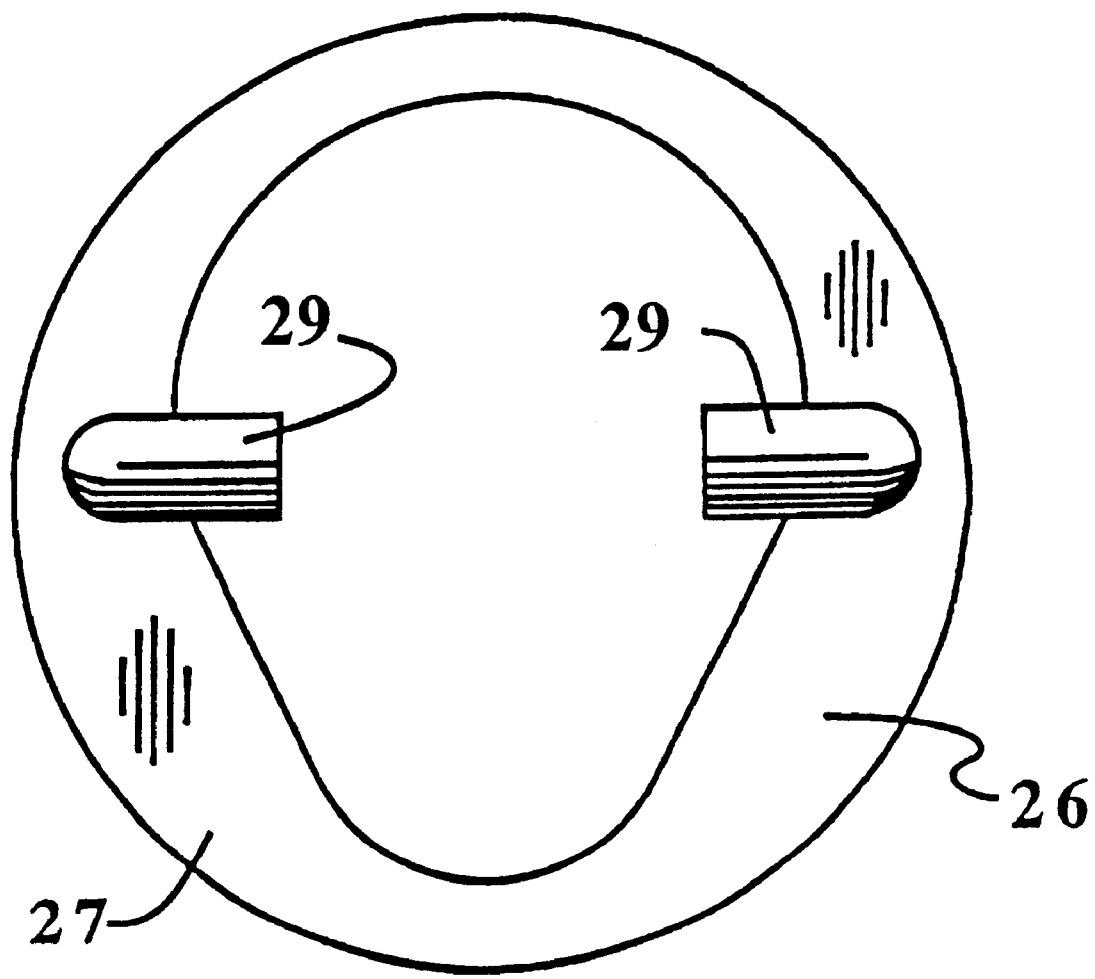
FIG. 5 is front view of the interconnection that is less flexible than the neck engaging portion and interconnection which is insert molded within the neck engaging portion.

FIG. 4 is a side view in cross section of the neck flange 11 of FIG. 3 or as would be seen if the cross section were taken along line 4—4 in FIG. 3 and the tracheostomy tube 10 were not included. The interconnection 26 is injection molded as an insert, the shape thereof is shown in FIG. 5, wherein the neck engaging portion 21 leaves the raised pair of opposed pins 29 exposed. That is, the interconnection 26 is made first with the preferred shape of the interconnection 26 as depicted in FIG. 5. The interconnection 26 is then inserted into an injection mold cavity, having the shape of the neck engaging portion 21; into that cavity the softer, more flexible polymer of the neck engaging portion 21 is injected. The resulting neck flange 11 is a combination of materials with the neck engaging portion 21 surrounding the interconnection 26. The cross sectional view of FIG. 4 shows the neck engaging portion 21 encapsulating the ring shaped body of the interconnection 26, and FIG. 3 shows that the pivot pins 29 are left unencapsulated.

As best illustrated in FIGS. 3 and 4 there are a pair of holes 30 in the neck engaging portion 21. The holes can be any shape; oval, elliptical or square; however, D shaped holes 30 are shown. Each D shaped hole 30 is spaced away from the interconnection 26 toward the edge 24 of the neck engaging portion 21, i.e. apart (laterally) from one another.

The pair of D shaped holes 30 are for attachment of a neck band (not shown) which is fit about the neck 12 to hold the tracheostomy tube 10 in the entry through the neck 12 of the patient. Although the D shaped holes 30 are preferred, any shape including those mentioned above, that would conveniently attach to a neck band can be used. The track 31 is shown with an inflated cuff 19 near the distal end 13.

What is claimed is:

1. A method for manufacturing a neck flange having a neck engaging portion of a flexible material and an interconnection of a less flexible material, the method having the following steps: molding a ring shaped interconnection of a polymer, and molding a neck engaging portion about the interconnection in a process by inserting the ring shaped interconnection into a mold before molding the neck engaging portion about the ring shaped interconnection.

2. The method of claim 1 wherein the molding process includes the steps of selecting polymers that are flexible and transparent so that the neck engaging portion is more flexible than the ring shaped interconnection.

* * * * *